United States Patent [19]

Brunke

[11] Patent Number: 4,762,819
[45] Date of Patent: Aug. 9, 1988

[54] 2,6-EXO CONFIGURED TRICYCLO-5.2.1.0$^{2,6}$ DECANE DERIVATIVES WITH FUNCTIONAL SIDE CHAINS AT C-8/C-9 AND THEIR UTILIZATION THEREOF AS PERFUMES

[75] Inventor: Ernst-Joachim Brunke, Holzminden, Fed. Rep. of Germany

[73] Assignee: Dragoco Gerberding & Co. GmbH, Fed. Rep. of Germany

[21] Appl. No.: 48,483

[22] Filed: May 5, 1987

Related U.S. Application Data

[63] Continuation of Ser. No. 658,199, filed as PCT EP84/00028 on Feb. 3, 1984 on Feb. 3, 1984, published as WO84/03086 on Aug. 16, 1984 abandoned.

[30] Foreign Application Priority Data

Feb. 5, 1983 [DE] Fed. Rep. of Germany ....... 3303893

[51] Int. Cl.$^4$ .................................................. A61K 7/46
[52] U.S. Cl. ....................................... 512/14; 512/18; 568/373; 568/445; 568/817
[58] Field of Search ............... 252/522 R; 568/373, 568/445, 817; 512/14, 18

[56] References Cited

U.S. PATENT DOCUMENTS

| | | | |
|---|---|---|---|
| 3,270,061 | 8/1966 | Chadraff et al. | 252/522 R |
| 3,542,877 | 11/1970 | Dunkel | 252/522 R |
| 3,557,188 | 1/1971 | Dunkel | 252/522 R |
| 3,598,745 | 8/1971 | Dunkel | 252/522 R |
| 4,123,394 | 10/1978 | Skorionety et al. | 568/817 |

FOREIGN PATENT DOCUMENTS

| | | | |
|---|---|---|---|
| 1416209 | 11/1964 | France | 252/522 R |
| 56-167631 | 12/1981 | Japan | 252/522 R |
| 58-18328 | 2/1983 | Japan | 252/522 R |
| 2020656 | 11/1979 | United Kingdom | 252/522 R |
| 2020277 | 11/1979 | United Kingdom | 252/522 R |

OTHER PUBLICATIONS

Kaster et al., J. Soc. Cosmet. Chem., vol. 37, pp. 404–428 (1986).

Primary Examiner—James H. Reamer
Attorney, Agent, or Firm—Hedman, Gibson, Costigan & Hoare

[57] ABSTRACT

The invention relates to 2,6-exo-configured tricyclo-5.2.1.0$^{2,6}$ decane derivatives that correspond to general formula A wherein

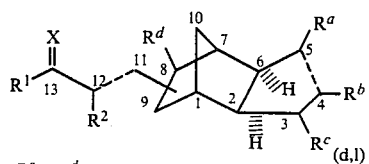

$R^a = R^b = R^c = R^d = H$
$R^a, R^b, R^c = H, CH_3$ (2 × H, 1 × CH$_3$), $R^d = CH_3$ $$X: = O, \begin{matrix} OH \\ \diagup \\ \diagdown \\ H \end{matrix}$$

$R^1, R^2$: H, C$_1$–C$_5$—Alkyl $R^a$, $R^b$, $R^c$, $R^d$ are hydrogen or $R^d$ is a methyl group and $R^a$, $R^b$, $R^c$ are hydrogen or methyl groups, one of the substituents being a methyl group and both the others being hydrogen, the broken line represents a C-C double bond optionally at (-3) or (-4), the wavy line represents geometric isomers, $R^1$ and $R^2$ are hydrogen, or lower alkyl groups with a total of 1-6 carbon atoms, and X represents a carbonyl or hydroxyl function, as well as a process for their synthesis and their use as scents.

13 Claims, 1 Drawing Sheet

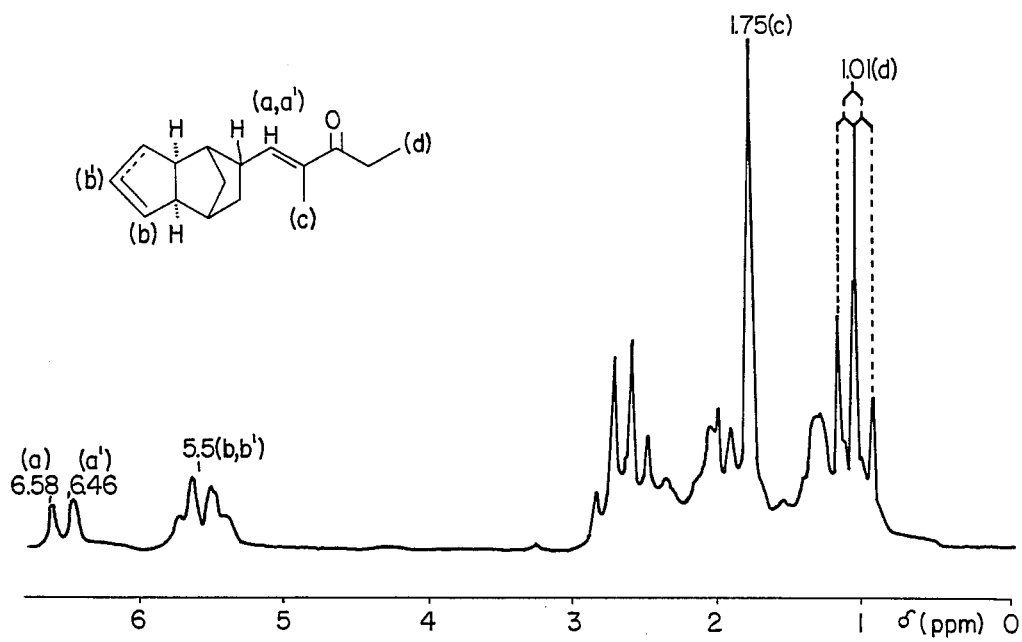
FIG.1 $^1$H-NMR-SPECTRUM (CCl$_4$, 60 MHz) OF 8
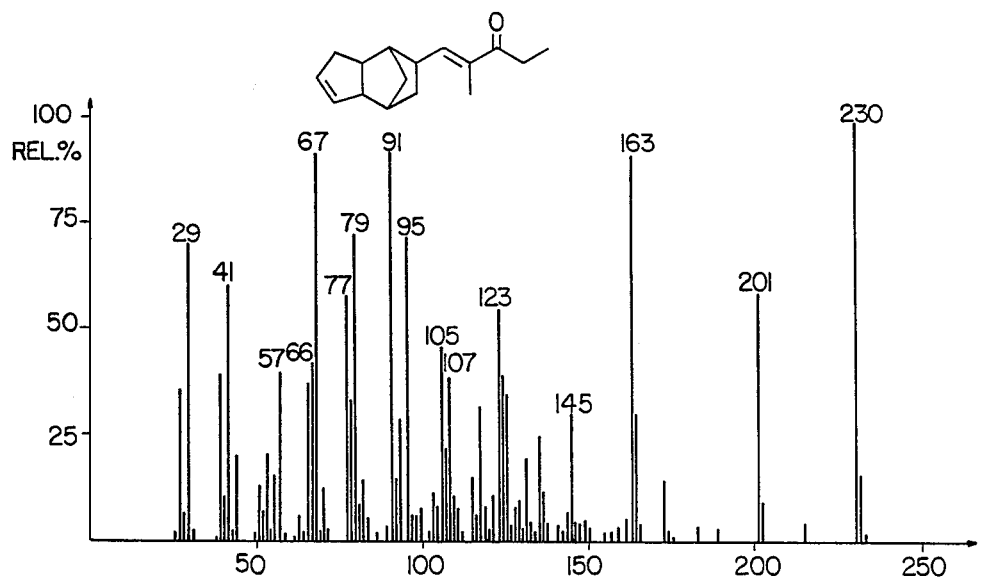
FIG.2 MASS SPECTRUM OF 8

2,6-EXO CONFIGURED TRICYCLO-5.2.1.0$^{2,6}$ DECANE DERIVATIVES WITH FUNCTIONAL SIDE CHAINS AT C-8/C-9 AND THEIR UTILIZATION THEREOF AS PERFUMES

This application is a continuation of Ser. No. 658,199, filed as PCT EP84/00028 on Feb. 3, 1984, published as WO84/03086 on Aug. 16, 1984, now abandoned.

DESCRIPTION

Dicyclopentadiene is, inter alia, an important starting material for the preparation of scent materials (review in: H. Abei, E. Baumgartner, H. P. Fiedler and G. Ohloff, "Kosmetika, Riechstoffe und Lebensmittelzusatzstoffe", G. Thieme Verlag, Stuttgart 1978, pp 55-57).

Among known scent materials with a tricyclo[5.2.1.0$^{2,6}$]-decane basic structure, few only have functional side chains. In German patent specification No. 1 218 643 (6/8/1966) the ring system saturated

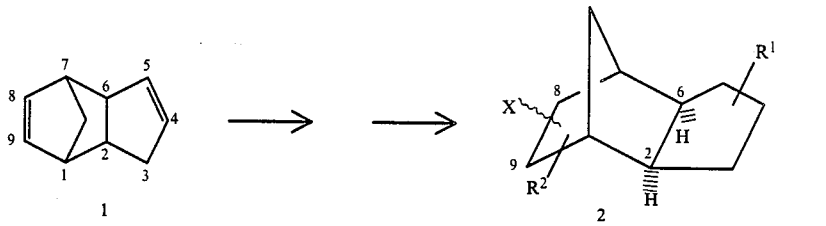

$R^1, R^2 =$ H, CH$_3$
$X =$ —O—CH—COOR
   (R = H, C$_1$-C$_4$—Alkyl)
   —CHO
   —CH=CH—CO—R'
   (R' = C$_1$-C$_5$—Alkyl)
   —CH$_2$—CH$_2$—CO—R'

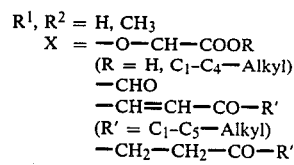

(8/9-exo, 2,6-endo)
R = C$_1$-C$_6$—Alkyl

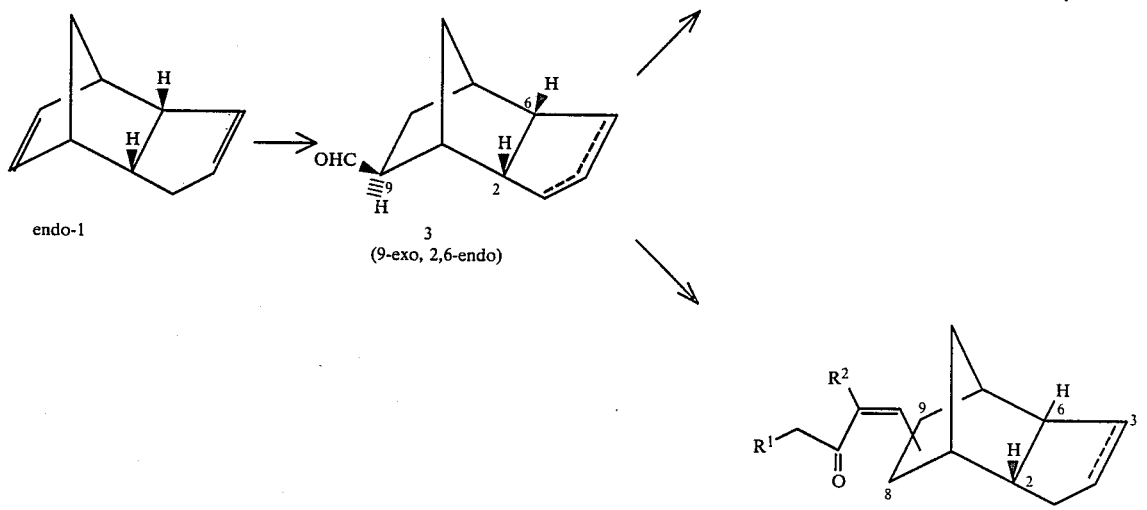

endo-1

3
(9-exo, 2,6-endo)

(8/9-exo, 2,6-endo)
$R^1, R^2 =$ H, C$_1$-C$_5$—Alkyl, C$_1$-C$_5$—Alkenyl tricyclodecane derivatives 2, in which the X group is a glycidate-, formyl- or straight-chain 3'-oxo-alkyl group, are claimed as scent materials. The ring connection at C-2 and C-6 should be of exo-configuration; nothing was said about the stereochemistry of the side chain connections at C-8 or C-9. The aldehyde of formula 2 possesses a fresh smell with an earthy note, and the unsaturated ketones of formula 2 have a smell of dried wood with a wine note (R=Me) or dried wood with a note of iris (R=Et).

By hydroformylization of the above endo-dicyclopentadienes (endo-1) at room temperature using a rhodium catalyst, aldehydes 3 with the relative 9-exo-2,6-endo-configuration are obtained [Y. Fujikura, Y. Inamoto, N. Takaishi and H. Ikeda, Synth. Commun., 6, 199–207 (1976)]. By condensation of these aldehydes 3 with aliphatic aldehydes, the unsaturated aldehydes 4 with exo-arrangement of the functional side chains and endo-ring connection at C-2 and C-6 are obtained; the broken line indicates an optical double-bond at C-3 [U.S. Pat. No. 4,229,324 (10/21/1980)]. Compounds of formula 4 possess a wood-type smell note with sub-notes of iris root and honey and can be used as scent materials.

By aldol condensation of 9-exo-2,6-endo-congured aldehydes with aliphatic aldehydes unsaturated ketones 5 are obtained having exo-arrangement of the functional side chains and endo-ring connections at C-2 and C-6; the broken line indicates an optional double bond at C-3 [French specification No. 2 425 419 (12/7/1979)]. The ketones of formula 5 described in this specification, occurring as geometric isomers, (double bond in the side chain) possess a woody smell note with an additional aspect of the type of iris root or honey.

Substances of the general formula A in accordance with the invention are distinguished from compounds of formula 5 (according to French No. 2 425 419) by the presence of the exo-configuration at C-2 and C-6 and from the compounds of formula 2 (according to German No. 1 218 643) by the presence of a double bond in the tricyclic ring system. The compounds of formula A are therefore novel.

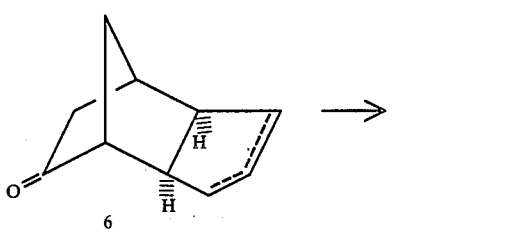

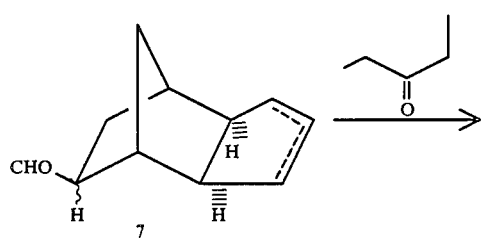

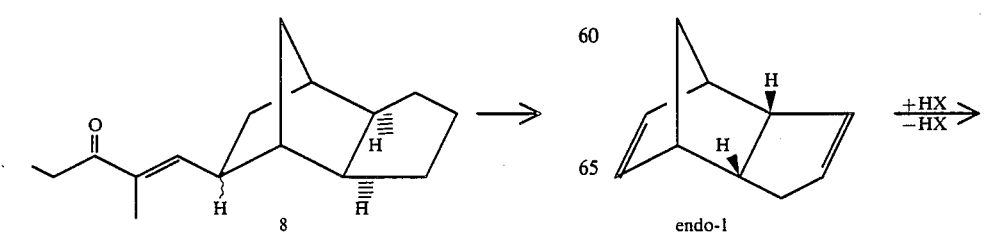

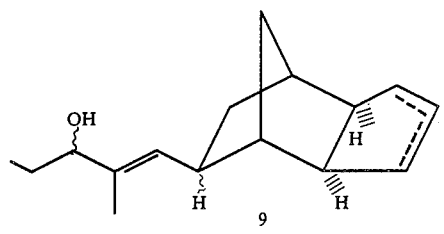

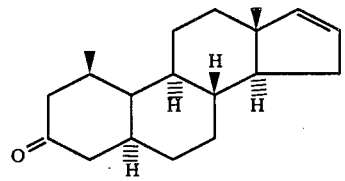

16-Androstene-3-one

Since the structure-varied compounds of the formulae 2, 4 and 5 steadily possess a woody smell note with a sub-note tending to iris plant or honey, it is astonishing that compounds of formula A show an animal-type odor note strongly differing therefrom. In particular, ketone 8, obtained by aldol condensation with diethyl ketone of the formyl-tricyclodecene 7 obtained by glycide ester synthesis of the known ketone 6, possesses an extremely intensive, urine-like animal note which resembles 16-androstene-3-one in intensity and small-type. By reduction of ketone 8 with sodium boron hydride or lithium aluminum hydride alcohol 9 is obtained having an animal-fat note which is reminiscent of sandalwood.

The preparation of compounds of general formula A ($R^a=R^b=R^c=R^d=H$) are obtained from dicyclopentadiene (1) in known manner by hydration under acid catalysis.

The next 2,6-endo-form dicyclopentadiene was thus isomerised in the 2,6-exo-form [G. L. Nelson and C. L. Kue, Synthesis, 105 (1975), H. P. Kaufman et al., "Fette, Seifen, Anstrichmittel", 67, 784 (1965)]. The corresponding ketone 6 obtained by oxidation [H. A. Bruson and Th. W. Reiner, J. Amer. Chem. Soc., 67, 723 (1945)] was converted to aldehyde 7 in known manner through glycide ester synthesis.

A further synthesis method for the preparation of 2,6-exo-configured aldehydes 7 begins with endo-dicyclopentadiene (endo-1) converted to exo-dicyclopentadiene (endo-1) in a manner analogous to the known disclosure [G. L. Nelson and Ch.-L. Kuo, Synthesis, 1975, 105]. Selective hydroformylization of the exo-1 analogous to the preparation of 3 [Y. Fujikura et al., Synth. Commun., 6, 199–207 (1976)] leads to 7.

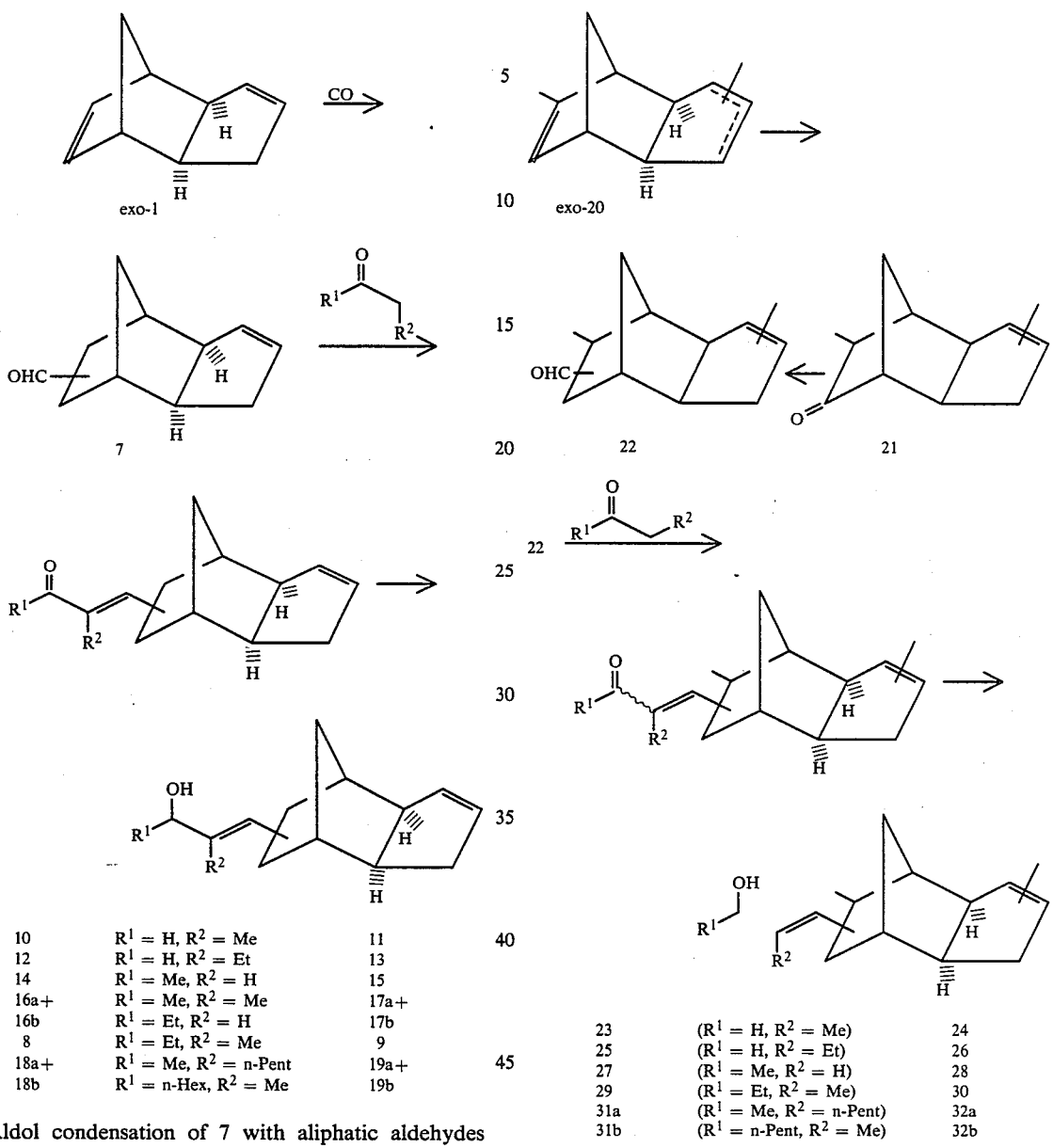

| | | | |
|---|---|---|---|
| 10 | R¹ = H, R² = Me | 11 | |
| 12 | R¹ = H, R² = Et | 13 | |
| 14 | R¹ = Me, R² = H | 15 | |
| 16a+ | R¹ = Me, R² = Me | 17a+ | |
| 16b | R¹ = Et, R² = H | 17b | |
| 8 | R¹ = Et, R² = Me | 9 | |
| 18a+ | R¹ = Me, R² = n-Pent | 19a+ | |
| 18b | R¹ = n-Hex, R² = Me | 19b | |

Aldol condensation of 7 with aliphatic aldehydes (e.g. propionaldehyde or butyraldehyde) gives unsaturated aldehydes 10 or 12, which can be reduced with lithium-aluminum hydride to unsaturated alcohols 11 or 13. The aldehydes 10,12 smell fresh, woody, sweet and the alcohols 11, 13 mild, woody-buttery with an aspect of sandalwood. By aldol condensation with acetone, methylethylketone, diethylketoen or methylhexylketone the unsaturated ketones 14, 16a,b, 8 or 18a,b (with animal, urine-like accents) are obtained which can be reduced to the unsaturated alcohols 15, 17a,b, 9 or 19a,b (with mild, woody-animal notes).

Proceeding from isomerised dimeric methylcyclopentadiene (exo-20) the higher homologs of formula A [$R^a$, $R^b$, $R^c$=H, $CH_3$ (2×H, $CH_3$), $R^d$=$CH_3$] can be prepared in an analogous way. Hydroformylization of isomerised dimethyldicyclopentadiene (isomeric mixture) or optionally glycide ester synthesis with the known ketone 21 (European patent specification No. A1 0 039 232) gives aldehydes 22.

| | | |
|---|---|---|
| 23 | (R¹ = H, R² = Me) | 24 |
| 25 | (R¹ = H, R² = Et) | 26 |
| 27 | (R¹ = Me, R² = H) | 28 |
| 29 | (R¹ = Et, R² = Me) | 30 |
| 31a | (R¹ = Me, R² = n-Pent) | 32a |
| 31b | (R¹ = n-Pent, R² = Me) | 32b |

Aldol condensation with the corresponding aliphatic aldehydes or ketones leads to the carbonyl compounds 23, 25, 27, 29 and 31a,b (with animal smell notes) and their reduction using sodium boron hydride or lithium aluminum-hydride results in alcohols 24, 26, 28, 30 and 32a,b (with sandalwood-like smell notes). Saturation of the tricyclic system by complete catalytic hydrogenation brings back considerable animal tonality.

Selective hydrogenation in the side chain of α,β-unsaturated carbonyl compounds 10, 12,14,16a,b, 8, 18a,b, 23,25,27, 29, 31a,b proceeds with use of Raney-nickel and alkaline components in methanol. The saturated carbonyl compounds 33, 35, 37, 39, 41 were converted to the corresponding alcohols 34, 36, 38, 40, 42 by reduction with sodium boron hydride. The carbonyl compounds 33, 35, 37, 39, 41 possess strong animal smell notes with waxy-fruity sub-notes. The alcohols 34, 36, 38, 40, and 42 smell mildly woody-animal in the direction of sandalwood. The dimethyl derivatives 43–52 obtained in a similar way from aldehyde 22 through the unsaturated carbonyl compounds 23, 25, 27, 29, 31a,b possess similar smell properties with somewhat greater fixation.

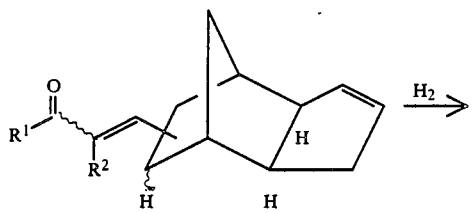

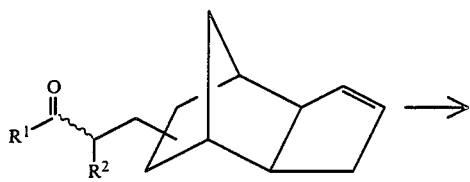

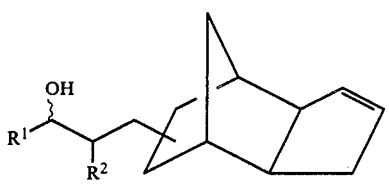

| 10 | 33 | (R¹ = H, R² = Me) | 34 |
| 12 | 35 | (R¹ = H, R² = Et) | 36 |
| 14 | 37 | (R¹ = Me, R² = H) | 38 |
| 16a | 39 | (R¹ = Me, R² = Me) | 40 |
| 8 | 41 | (R¹ = Et, R² = Me) | 42 |

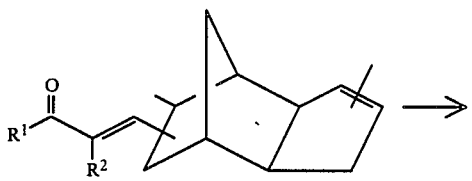

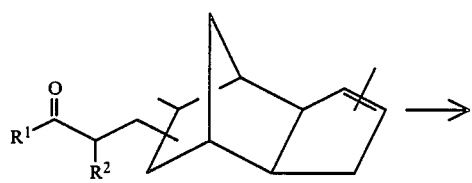

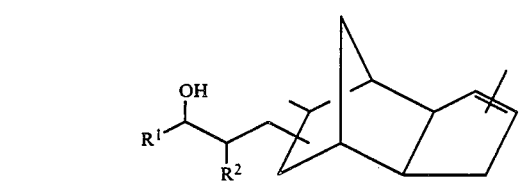

| 23 | 43 | R¹ = H, R² = Me | 44 |
| 25 | 45 | R¹ = H, R² = Et | 46 |
| 27 | 47 | R¹ = Me, R² = H | 48 |
| 29 | 49 | R¹ = Me, R² = Me | 50 |
| 31a,b | 51 | R¹ = Et, R² = Me | 52 |

Physical data of the compounds described above are summarised in the following table.

| | $D_4^{20°}$ | $n_D^{20°}$ | | $D_4^{20°}$ | $n_D^{20°}$ |
| --- | --- | --- | --- | --- | --- |
| 10 | 1.0426 | 1.5382 | 33 | 1.0103 | 1.5045 |
| 11 | 1.0831 | 1.5291 | 34 | 1.0091 | 1.5022 |
| 14 | 1.0579 | 1.5322 | 37 | 1.0563 | 1.5298 |
| 15 | 1.0631 | 1.5291 | 38 | 1.0621 | 1.5200 |
| 16a, b | 1.0291 | 1.5287 | 39 | 1.0135 | 1.5205 |
| 17a, b | 1.0226 | 1.5214 | 40 | 0.9905 | 1,5173 |
| 8 | 1.0149 | 1.5252 | 41 | 0.9975 | 1.5096 |
| 9 | 0.9817 | 1,5050 | 42 | 0.9932 | 1.5105 |
| 18a, b | 0.9946 | 1,5120 | 43 | 1.0073 | 1.5105 |
| 19a, b | 0.9950 | 1,5159 | 44 | 1.0105 | 1.5076 |
| 23 | 0.9961 | 1.5131 | 47 | 0.9931 | 1.5013 |
| 24 | 0.9992 | 1,5096 | 48 | 0.9895 | 1.5075 |
| 27 | 1.0161 | 1.5213 | 51 | 0.9916 | 1.5006 |
| 28 | 1.0310 | 1.5192 | 52 | 0.9884 | 1,5062 |
| 29 | 1.0075 | 1.5195 | | | |
| 31a, b | 0.9932 | 1.5130 | | | |
| 32a, b | 0.9871 | 1.5032 | | | |

BRIEF DESCRIPTION OF THE DRAWING

FIG. 1 is the NMR spectra of the compound of Example 2.

FIG. 2 is the mass spectrum of the compound of Example 2.

The preparatory examples 1–7 contain reaction conditions by means of which all compounds of general formula A can be prepared.

Compounds of the general formula A can be used advantageously as scent materials because of their smell properties. The following typical use examples illustrate the invention without limiting it.

EXAMPLE 1

Preparation of 8-formyl-2,6-exo-tricyclo[5.2.1.0$^{2,6}$]decene-4 (3) (7)

A solution of 444 g (3 mol) 6, 550 g (4.5 mol) chloracetic ethyl ester and 1.5 g phenothiazine in 300 ml pyridine were added portionwise while stirring at −5° to −10° C. to 270 g (5.0 mol) sodium methylate. Next 300 ml ether were run in. After 4 hours stirring at −5° C. 1.4 l 15% methanolic caustic soda was added. It was stirred for a further 10 hours at 0° C., neutralised with 1.5 l acetic acid, diluted with 2.0 l water, extracted several times with ether and worked out. By concentration of the combined organic phases 550 g of endproduct were obtained (dark yellow oil) that according to GC consisted of 70% 7 and 30% 6.

IR (film): $\nu$=2700, 1720 cm$^{-1}$ (aldehyde). $^1$H-NMR (CCl$_4$): $\delta$=5.3–5.8, m (olefinic H), 9.61 and 9.95 ppm, 2 "s" (—CHO). MS: m/z (%)=162 (41, M$^+$), 144 (8), 133 (6), 129 (12), 118(67), 105 (62), 96 (41), 91 (48), 77 (45), 67 (100). C$_{11}$H$_{14}$O (162.2).

EXAMPLE 2

Preparation of 2'-methyl-3-oxo-pent-1'-enyl-2,6-exo-tricyclo[5.2.1.0$^{2,6}$]decene-4(3) (8)

A solution of 178 g 7 (70%, endproduct of Example 1) and 95 g diethyl ketone in 400 ml methanol were added dropwise with stirring at 0° C. over about 15 minutes to 40 ml caustic soda (33%). It was left standing at room temperature for 3 hours and stirred for 30 minutes at boiling temperature. After cooling 100 g acetic acid were added. It was confined, taken in about 300 ml water, extracted with petroleum ether and worked out. The end-product (200 g brown oil) was distilled over a 30 cm Vigreux column. It yielded 105 g (60%) 8 as a colorless oil [BP (0.4 mbar)=120° C.] with a strong urine-like smell.

IR (film): 1680, 1640 cm$^{-1}$ ($\alpha,\beta$ unsaturated ketone). $^1$H-NMR: FIG. 1, MS: FIG. 2. $C_{16}H_{22}O$ (230.4).

EXAMPLE 3

Preparation of
2′methyl-3′-hydroxy-pent-1′-enyl-2,6-exo-tricyclo[5.2.1.0$^{2,6}$]decene-4(3) (9)

A solution of 5 g sodium boron hydride and 0.1 g sodium hydroxide in 10 ml water were dropped internally over 20 minutes into a solution of 23 g (0.1 mol) of ketone 8 in 15 ml ethanol. After 3 hours stirring at room temperature 200 ml water were added and extracted with ether. The combined organic phases were neutral-washed, separated and distilled over a 30 cm Vigreux column. This yielded 15 g (65%) 9 as a colorless oil [BP (0.5 mbar)=118°–120° C.] with a buttery, sandalwood-like smell.

IR (film): 3380 cm$^{-1}$ (OH). $^1$H-NMR (CCL$_4$): $\delta$=0.78, t, J=7 Hz (—CH$_2$CH$_3$), 1.60, br.s (2′—CH$_3$), 3.75, br.t, J=6 hz (—CH(OH)—), 5.15, m (olefinic 1′H), 5.25–5.75 ppm, m (olefinic 3-, 4-, 5-H). MS: m/z (%)=232 (3, M$^+$), 214 (2), 203 (79), 185 (16), 175 (9), 149 (66), 147 (36), ..., 99 (94), 91 (67), 79 (70), 67 (100). $C_{16}H_{24}O$ (232.4).

EXAMPLE 4

Preparation of
2′-formyl-prop-1′enyl-2,6-exo-tricyclo[5.2.1.0$^{2,6}$]decene-5(3) (10)

6.0 g sodium methylate were added at 10° C. to a solution of 162 g 7 (70%, end-product of Example 1). While stiring 64 g propionaldehyde were dropped in internally over 1 hour. After 5 minutes stirring at boiling temperature and subsequent cooling it was neutralised with acetic acid. After usual working out the obtained product (220 g) was distilled over a 15 cm Vigreux column. This yielded 132 g (65%) 10 as a colorless oil; BP (1 mbar)=018°–110° C.

IR (film): 2702, 1685, 1635 cm$^{-1}$ ($\alpha,\beta$ unsaturated aldehyde), $^1$H-NMR: 67=1.73, d, J=2.5 Hz (olefinic methyl), 5.3–5.8, m (olefinic 3-, 4-, 5-H), 6.18 and 6.33, 2m (olefinic 1-H, 9-exo-/9-endo-), 927 ppm (—CHO). MS: m/z (%)=202 (37, M$^+$), 187 (3), 173 (9), 136 (35), 135 (74), 131 (13), 117 (34) 106 (86), 105 (82), 97 (51), 95 (53), 91 (100). $C_{14}H_{18}O$ (202.3),

EXAMPLE 5

Preparation of
3′-hydroxy-2′-methyl-prop-1′enyl-2,6-exo-tricyclo[5.2.1.0$^{2,6}$]decene-4(3) (11)

With stirring at room temperature a solution of 34 g (0.2 mol) 10 in 50 ml ether was dropped into a suspension of 2.5 g (0.07 mol) lithium aluminum hydride in 120 ml ether. After 3 hours stirring at boiling temperature first was added 5 ml ethyl acetate and then 10 ml water and worked out. Distillation over a 15 cm Vigreux column gave 29.5 g (87%) 11 as a colorless oil; BP (1 mm)=123° C.

IR (film): 3400 cm$^{-1}$ (OH). NMR (CCl$_4$): $\delta$=1.63, d, J=2 Hz (olefinic CH$_3$), 3.79, br.s (—CH$_2$—OH), 5.12, m (olefinic 1′-H), 5.2–5.7 ppm (olefinic 3-, 4-, 5-H). MS: m/z (%)=204 (5, M$^+$), 189 (4), 186 (2), 173 (18), 149 (100), 137 (12), 151 (16), 119 (25), 107 (27), 105 (30), 91 (62), 79 (83), 67 (76). $C_{14}H_{20}O$ (204.3).

EXAMPLE 6

2′-methyl-3′-oxo-butyl-2,6-exo-tricyclo[5.2.1.0$^{2,6}$]decene-4(3) (41) by selective hydrogenation A solution of 43.2 g (0.2 mol) 16a (analogous with example 2) and 0.4 g sodium hydroxide in 240 ml methanol were mixed with 0.8 g Raney-nickel and shaken for 7 hours in a hydrogen atmosphere (room temperature, normal pressure); 4.44 l of hydrogen were taken up (theoretical take-up 4.48 l). Filtration, separation and working up gave 44 g end-product that was distilled over a 1 m rotatable column. It yielded 34.5 g colorless oil, BP (0.5 mbar)=86° C., that according to gas chromatography consisted of about 70% of the selectively hydrogenated ketone 39 and up to about 30% of the corresponding fully hydrogenated ketone.

39: IR (Film): $\nu$=1702 cm$^{-1}$ (saturated ketone). $^1$H-NMR (CCl$_4$): $\delta$=1.03, d, J=7 Hz (2′—CH$_3$), 2.02 p (CH$_3$—4′), 5.30–5.65 ppm, m (CH—3.4). MS: m/z (%)=218 (10, M$^+$), 200 (3), 175 (5), 151 (46), 147 (100), 146 (18), 133 (20), 79 (75), 67 (78), 66 (78), ..., 43 (36). $C_{15}H_{22}O$ (218.2).

EXAMPLE 7

Preparation of
2′-methyl-3′-hydroxy-butyl-2,6-exo-tricyclo[5.2.1.0$^{2,6}$]-decene-4 (3) (40)

A solution of 30 g (0.136 mol) 39 (according to Example 6) in 150 ml diethyl ether was added dropwise while stirring to 2.7 g (0.07 mol) lithium aluminum hydroxide in 100 ml diethylether. After 2 hours stirring at boiling temperature it was carefully mixed with ethyl acetate and worked up. The end-product was distilled over a 20 cm-Vigreux column. It yielded 24 g (78%) 40 as a colorless oil, BP (2 mbar)=130°–133° C.

IR (Film): $\nu$=3350 cm$^{-1}$ (hydroxy-). $^1$H-NMR: $\delta$=0.87 and 0.93 (CH$_3$—4′), 1.04, d, J=7 Hz (2′—CH$_3$), 3.3–3.6, m (CH—3.4). MS: m/z (%)=220 (8, M$^+$), 153 (32), 135 (53), 131 (15), 117 (11), 107 (27); 105 (13), 93 (33), 91 (31), 81 (22), 80 (44), 79 (56), ..., 67 (87), 66 (100). $C_{15}H_{24}O$ (220.3).

EXAMPLE 8

| Perfume oil with flowery-aldehyde-like note | |
|---|---|
| α-hexylcinnamaldehyde | 200 |
| phenylethyl alcohol | 140 |
| acetyl cedrene | 100 |
| vetiveryl acetate | 80 |
| hydroxycitronellal | 80 |
| γ-methylionone | 80 |
| citronella oil | 60 |
| benzyl acetate | 50 |
| geraniol | 50 |
| oil of bergamot, Reggio | 50 |
| trichlormethylphenylcarbinyl acetate | 20 |
| coumarin | 20 |
| ambrette musk | 20 |
| ketone musk | 20 |
| cyclopentadecanolide | 9 |
| | 999 |

This perfume oil possesses a weighty flowery-aldehyde-like smell character with a rough, woody base.

(a) By addition of 1 part of a 10% solution of ketone 8 or ketone 29 in dipropylene glycol the perfume oil obtains a very desirable animal aspect which is reminiscent of civet or tonka musk.

(b) By addition of 1 parts of the aldehyde 10 or the aldehyde 23 the woody-animal base is emphasised.

EXAMPLE 9

| Perfume base of the sandalwood type | |
|---|---|
| cedrene | 80 |
| acetyl cedrene | 350 |
| compound 9 | 350 |
| oil of amyris | 200 |
| compound 8 | 20 |
| (1% in dipropylene glycol) | |
| | 1000 |

This perfume base possesses a pronounced animal-woody smell of sandalwood type.

EXAMPLE 10

| Perfume oil with lily of the valley smell | |
|---|---|
| hydroxycitronellal | 200 |
| phenylethyl alcohol | 200 |
| α-hexylcinnamaldehyde | 200 |
| linalool | 100 |
| oil of citronella | 80 |
| hydroxyisohexyltetrahydrobenzaldehyde | 30 |
| linalyl acetate | 25 |
| oil of rosewood | 25 |
| geraniol | 20 |
| ylang-ylang oil | 15 |
| benzyl acetate | 10 |
| phenylacetaldehyde-dimethylacetate | 10 |
| oil of cinnamon, 10% in diethylphthalate | 10 |
| indole, 10% in diethylphthalate | 10 |
| heptanal, 10% in diethylphthalate | 5 |
| | 940 |

Addition of about 60 parts of compound 11 or 24 imparts to the perfume oil with lily of the vally smell a mild woody note and improves fixation.

EXAMPLE 11

| Perfume oil with sweet-balsam note | |
|---|---|
| phenylethyl alcohol | 180 |
| Singapore patchouli oil | 120 |
| oil of bergamot | 90 |
| hydroxycitronellal | 70 |
| γ-methylionone | 60 |
| ketone musk | 60 |
| ambrette musk | 50 |
| α-hexylcinnamaldehyde | 50 |
| eugenol | 40 |
| French oil of lavender | 40 |
| ethylvanillin, 10% in dipropylene glycol | 30 |
| Siamese benzoin resinoid | 25 |
| phenylethylacetate | 25 |
| benzyl acetate | 25 |
| coumarin | 25 |
| Bourbon oil of geranium | 25 |
| Peru balsam oil | 20 |
| ethylene brassylate | 15 |
| isoeugenol | 10 |
| camomile oil | 10 |
| | 970 |

By addition of 30 parts of ketone mixtures 18a+18b or 31a+31b an accentuation of the dark-balsam note is obtained with simultaneous rounding-off.

I claim:

1. 2,6-exo-configured tricyclo[5.2.1.0$^{2,6}$]decane derivatives ot the general formula A,

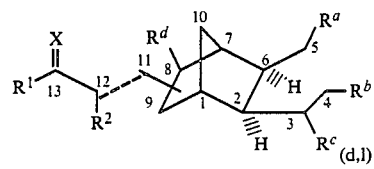

wherein $R^a$, $R^b$, $R^c$ and $R^d$ are hydrogen or $R^d$ is a methyl group and $R^a$, $R^b$, $R^c$ are hydrogen or methyl groups of which one of the substituents is a methyl group and both of the others are hydrogen, the broken line between C11/C12 indicates a C—C double bond or a C—C single bond, $R^1$ and $R^2$ are hydrogen, or a straight-chain or branched-chain $C_1$-$C_6$ lower alkyl group, and X displays a carbonyl or hydroxyl function.

2. A compound as defined in claim 1 which has the formula:

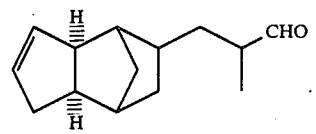

3. A compound as defined in claim 1 which has the formula

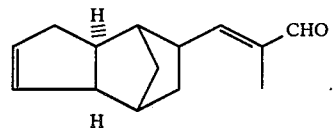

4. A compound as defined in claim 1 which has the formula:

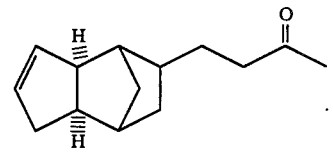

5. A compound as defined in claim 1 which has the formula:

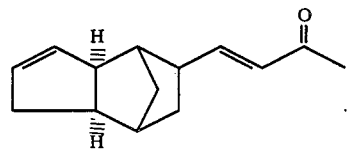

6. A compound as defined in claim 1 which has the formula:

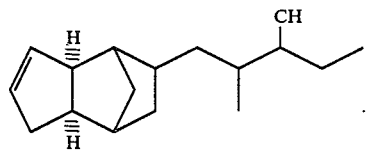

7. A compound as defined in claim 1 which has the formula:

8. A compound as defined in claim 1 which has the formula:

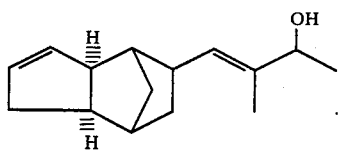

9. A compound as defined in claim 1 which has the formula:

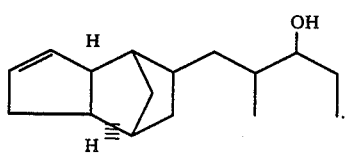

10. A compound as defined in claim 1 which has the formula:

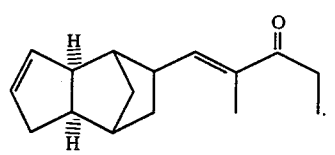

11. A compound as defined in claim 1 which has the formula:

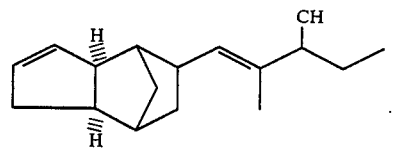

12. A compound as defined in claim 1 which has the formula:

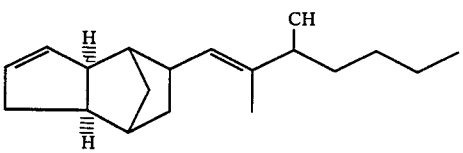

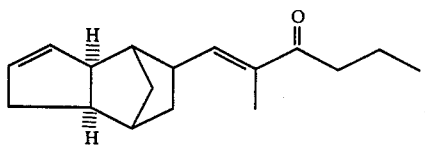

13. Use of compounds defined in claim 1 as scents or components of scent mixtures or perfume oils for cosmetic or industrial perfuming.

* * * * *